United States Patent
Beliaev et al.

(10) Patent No.: US 8,957,222 B2
(45) Date of Patent: *Feb. 17, 2015

(54) PROCESS FOR PREPARING INTERMEDIATES OF PERIPHERALLY-SELECTIVE INHIBITORS OF DOPAMINE-β-HYDROXYLASE INVOLVING CATALYTIC ASYMMETRIC HYDROGENATION

(75) Inventors: Alexander Beliaev, Mindelo (PT); David Alexander Learmonth, Alfena (PT); Wenge Li, Plainsboro, NJ (US)

(73) Assignee: Bial-Portela & CA, S.A., S. Mamede do Coronado (PT)

( * ) Notice: Subject to any disclaimer, the term of this patent is extended or adjusted under 35 U.S.C. 154(b) by 975 days.

This patent is subject to a terminal disclaimer.

(21) Appl. No.: 12/921,966

(22) PCT Filed: Mar. 17, 2009

(86) PCT No.: PCT/PT2009/000014
§ 371 (c)(1), (2), (4) Date: Jan. 13, 2011

(87) PCT Pub. No.: WO2009/116883
PCT Pub. Date: Sep. 24, 2009

(65) Prior Publication Data
US 2011/0112303 A1 May 12, 2011

Related U.S. Application Data

(60) Provisional application No. 61/037,784, filed on Mar. 19, 2008.

(51) Int. Cl.
| | | |
|---|---|---|
| C07D 235/02 | (2006.01) | |
| C07D 233/84 | (2006.01) | |
| C07F 15/00 | (2006.01) | |
| C07D 311/04 | (2006.01) | |
| C07D 405/04 | (2006.01) | |

(52) U.S. Cl.
CPC ............ *C07D 311/04* (2013.01); *C07D 405/04* (2013.01); *C07F 15/0053* (2013.01); *C07F 15/008* (2013.01)
USPC ..................... 548/302.7; 548/311.1; 549/208; 549/212; 556/136

(58) Field of Classification Search
None
See application file for complete search history.

(56) References Cited

U.S. PATENT DOCUMENTS

| | | |
|---|---|---|
| 5,144,050 A | 9/1992 | Chan et al. |
| 6,521,769 B1 | 2/2003 | Zhang |
| 6,855,657 B2 * | 2/2005 | Zhang .................. 502/166 |

FOREIGN PATENT DOCUMENTS

| | | |
|---|---|---|
| EP | 1214328 B1 | 5/2006 |
| WO | 0121625 A1 | 3/2001 |

(Continued)

OTHER PUBLICATIONS

Transition Metals in the Synthesis of Complex Organic Molecules (2nd ed.), Louis Hegedus (1999), p. 5.*

(Continued)

*Primary Examiner* — Michael Barker
*Assistant Examiner* — Po-Chih Chen
(74) *Attorney, Agent, or Firm* — Conley Rose, P.C.; Rodney B. Carroll

(57) ABSTRACT

A process for preparing the S or R enantiomer of a compound of formula A,

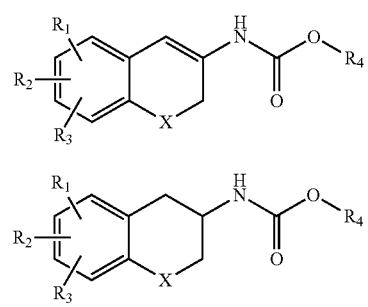

the process comprising subjecting a compound of formula B to asymmetric hydrogenation in the presence of a chiral transition metal catalyst and a source of hydrogen, wherein X is $CH_2$, oxygen, or sulphur; $R_1$, $R_2$ and $R_3$ are the same or different and signify hydrogens, halogens, alkyl, alkyloxy, hydroxy, nitro, alkylcarbonylamino, alkylamino, or dialkylamino group; and $R_4$ is alkyl or aryl, wherein the transition metal catalyst comprises a chiral ligand having the formula

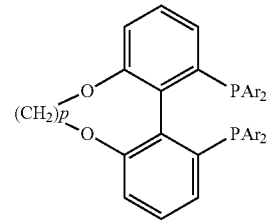

wherein p is from 1 to 6, and Ar means aryl group; wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means an aromatic or heteroaromatic group, optionally substituted by alkyloxy, halogen, or nitro group; and the term halogen means fluorine, chlorine, bromine, or iodine.

32 Claims, No Drawings

(56) References Cited

FOREIGN PATENT DOCUMENTS

| WO | 0240491 A1 | 5/2002 |
| WO | 2004033447 A1 | 4/2004 |
| WO | 2009/116883 A2 | 9/2009 |
| WO | 2009/116883 A3 | 9/2009 |
| WO | 2009/116883 A8 | 9/2009 |

OTHER PUBLICATIONS

Gorobets et al., Tetrahedron Letters 2005, 46, 3843-3846.*

EP Examination Report, EP Application No. 09 721 339.1, Nov. 7, 2011, 3 pages.

Lei, Aiwen, et. al., "Highly enantioselective asymmetric hydrogenation of α-phthalimide ketone: an efficient entry to enantiomerically pure amino alcohols", J. Am. Chem. Soc., 2004, vol. 126, No. 6, pp. 1626-1627, American Chemical Society.

Dupau, Philippe, et al., "New route to optically active amine derivatives: ruthenium-catalyzed enantioselective hydrogenation of ene carbamates," Tetrahedron: Asymmetry, 1999, vol. 10, pp. 3467-3471, Elsevier Science Ltd, XP-002476034.

Foreign communication from the priority application—International Search Report and Written Opinion, PCT/PT2009/000014, 14 pages, Feb. 15, 2010.

Foreign communication from the priority application—International Preliminary Report on Patentability, PCT/PT2009/000014, 6 pages, Sep. 21, 2010.

* cited by examiner

PROCESS FOR PREPARING INTERMEDIATES OF PERIPHERALLY-SELECTIVE INHIBITORS OF DOPAMINE-β-HYDROXYLASE INVOLVING CATALYTIC ASYMMETRIC HYDROGENATION

CROSS-REFERENCE TO RELATED APPLICATIONS

This application is a filing under 35 U.S.C. 371 of International Application No. PCT/PT2009/000014 filed Mar. 17, 2009, entitled "Process," which is a non-provisional of and claims priority to U.S. Provisional Patent Application No. 61/037,784 filed on Mar. 19, 2008, which applications are incorporated by reference herein in their entirety.

BACKGROUND OF THE INVENTION

The present invention relates to an improved catalytic process for asymmetric hydrogenation. In particular, the present invention relates to a process for preparing intermediates useful in the synthesis of peripherally-selective inhibitors of dopamine-β-hydroxylase, the process involving catalytic asymmetric hydrogenation. The present invention also relates to advantageous ligands, and novel catalysts incorporating the ligands, for use in the hydrogenation.

(R)-5-(2-Aminoethyl)-1-(6,8-difluorochroman-3-yl)-1,3-dihydroimidazole-2-thione hydrochloride (the compound of formula 1, below) is a potent, non-toxic and peripherally selective inhibitor of DβH, which can be used for treatment of certain cardiovascular disorders. Compound 1 is disclosed in WO2004/033447, along with processes for its preparation.

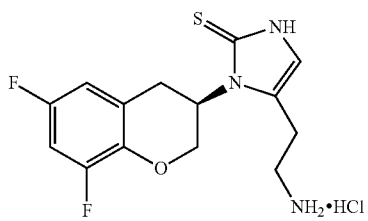

1

The process disclosed in WO02004/033447 involves the reaction of (R)-6,8-difluorochroman-3-ylamine hydrochloride (the structure of (R)-6,8-difluorochroman-3-ylamine is shown below as compound 2), [4-(tert-butyldimethylsilanyloxy)-3-oxobutyl]carbamic acid tert-butyl ester and potassium thiocyanate.

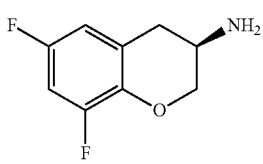

2

(R)-6,8-difluorochroman-3-ylamine (compound 2) is a key intermediate in the synthesis of compound 1. The stereochemistry at the carbon atom to which the amine is attached gives rise to the stereochemistry of compound 1, so it is advantageous that compound 2 is present in as pure a form as possible. In other words, the R enantiomer of compound 2 should be in predominance, with little or no S enantiomer present. Thus, the process for preparing compound 2 will advantageously produce compound 2 with as high an enantiomeric excess as possible.

BRIEF SUMMARY OF THE INVENTION

An advantageous process for preparing a precursor of, for example, the compound of formula 2 has now been found. The process involves catalytic asymmetric hydrogenation of a corresponding ene-carbamate using a transition metal complex comprising a chiral ligand having the formula, wherein p is from 1 to 6, and Ar means aryl group.

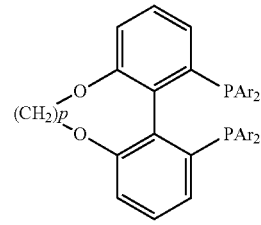

Such ligands and processes for their production are described in EP1214328A. The process may also be employed in the preparation of similar precursors useful in the production of other peripherally-selective inhibitors of dopamine-β-hydroxylase. The catalyst is particularly advantageous as it shows high activity and selectivity in the asymmetric hydrogenation reaction. Levels of activity and selectivity have also been shown to be improved when the hydrogenation is carried out in the presence of acid additives. Furthermore, the catalysts have been shown to be highly effective when hydrogenation is carried out on a large scale, which makes the catalysts highly suitable for industrial use. More specifically, it has been found that, in an embodiment, with 950g substrate and a substrate/catalyst ratio of 4000:1, the desired chiral product was obtained with an optical purity greater than 99.9% and in a yield of 90%. It has also been found that, in an embodiment, with 5000g substrate and a substrate/catalyst ratio of 3000:1, and following re-crystallization from IPA and water, the desired chiral product was obtained with an optical purity greater than 99%, chemical purity greater than 99% and in a yield of 88%.

DETAILED DESCRIPTION OF THE INVENTION

According to a first aspect of the present invention, there is provided a process for preparing the S or R enantiomer of a compound of formula A,

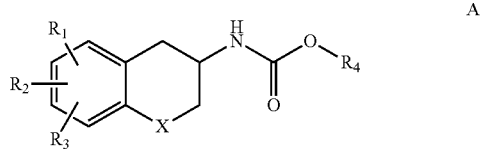

A the process comprising subjecting a compound of formula B to asymmetric hydrogenation in the presence of a chiral transition metal catalyst and a source of hydrogen,

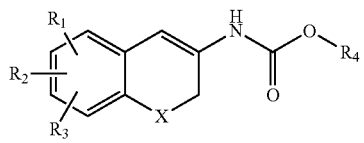

wherein X is CH$_2$, oxygen or sulphur; R$_1$, R$_2$ and R$_3$ are the same or different and signify hydrogens, halogens, alkyl, alkyloxy, hydroxy, nitro, alkylcarbonylamino, alkylamino or dialkylamino group; and R$_4$ is alkyl or aryl, wherein the transition metal catalyst comprises a chiral ligand having the formula,

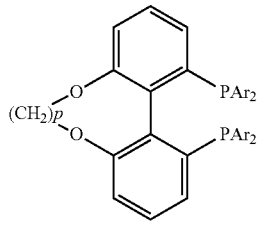

wherein p is from 1 to 6, and Ar means aryl group, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means aromatic or heteroaromatic group, optionally substituted by alkyloxy, halogen or nitro group; and the term halogen means fluorine, chlorine, bromine or iodine. In an embodiment, the term aryl may mean an aromatic ring comprising from 4 to 8 atoms and optionally comprising from 1 to 3 heteroatoms. Suitably, aryl means phenyl or naphthyl.

The chiral ligands used in the process of the present invention are from a series of ligands known under the name "TunePhos." Throughout this specification, references to the "TunePhos" series of ligands refer to the chiral ligands having the formula defined above. Compound B may be referred to as an ene-carbamate.

In an embodiment, the source of hydrogen is hydrogen gas.

In an embodiment, X is O. In another embodiment, at least one of R$_1$, R$_2$ and R$_3$ is halogen, preferably fluorine. Preferably, two of R$_1$, R$_2$ and R$_3$ are halogen, preferably fluorine, and the other of R$_1$, R$_2$ and R$_3$ is hydrogen.

Suitably, compound A has the following formula:

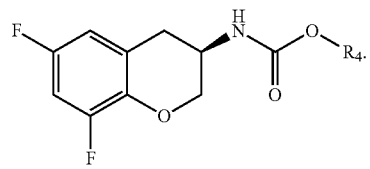

In an embodiment, R$_4$ is C$_1$ to C$_4$ alkyl. Optionally, R$_4$ is methyl (i.e. the methyl-substituted carbamate), ethyl (i.e. the ethyl-substituted carbamate) or $^t$Bu (i.e. the $^t$Bu-substituted carbamate). Preferably, R$_4$ is methyl. In an alternative embodiment, R$_4$ is benzyl (i.e. the benzyl-substituted carbamate).

The chiral transition metal complex comprises a chiral ligand selected from the TunePhos series of ligands. The TunePhos series of ligands have the following general formula:

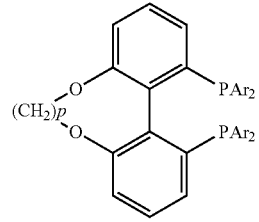

where p is an integer from 1 to 6, and Ar means aryl group. Suitably, Ar is phenyl. When Ar is phenyl, the TunePhos ligands are called Cp TunePhos, wherein p has the same meaning as above. For example, when p is 1 and Ar is phenyl, the ligand is called C1 TunePhos, and when p is 4 and Ar is phenyl, the ligand is called C4 TunePhos, and so on. The TunePhos ligand may be in the form of the R enantiomer or the S enantiomer. Preferred ligands from the TunePhos series are the R and S enantiomers of C1, C2, C3, C4, C5 and C6 TunePhos. Preferably, the ligand is the R or S enantiomer of C3 TunePhos, most preferably the S enantiomer.

In an embodiment, the catalyst is a ruthenium-based catalyst. The catalyst may comprise auxiliary ligands, i.e., ligands other than the chiral ligand. Suitably, the catalyst has the formula [(TunePhos)Ru(arene)X']Y, [(TunePhos)Ru(L)$_2$] or [(TunePhos)Ru(L')$_2$X'$_2$], wherein X' is a singly-negative monodentate ligand, Y is a balancing anion, L is a monovalent negative coordinating ligand and L' is a non-ionic monodentate ligand.

In an embodiment, X' is chloride. In another embodiment, Y is chloride. Both X' and Y may be chloride. In another embodiment, arene is p-cymene or benzene. L may be acac (i.e., acetylacetonate), CF$_3$COO or BF$_4$. Suitably, L' is dmf. Other options for the ligands include acetate, trifluoroacetate, tetrafluoroborate, and mono- and diamine salts such as secondary amines including Me$_2$NH$_2^+$ and Et$_2$NH$_2^+$.

Suitable catalysts include [Ru(p-cymene)(TunePhos)Cl]Cl, [Ru(TunePhos)Cl]$_2$(μ-Cl)$_3$(Me$_2$NH$_2$), [Ru(TunePhos)Cl]$_2$(μ-Cl)$_3$(Et$_2$NH$_2$), Ru(TunePhos)(BF$_4$)$_2$, Ru(TunePhos)(OAc)$_2$, Ru(TunePhos)(acac)$_2$, Ru(TunePhos)(CF$_3$COO)$_2$ and Ru(Tune Phos)Cl$_2$(dmf)$_m$ wherein m is 2, 3 or 4. Preferred catalysts are Ru(TunePhos)(acac)$_2$ and Ru(TunePhos)(CF$_3$COO)$_2$. Preferred TunePhos ligands for inclusion in the preferred catalysts are C3-, C4- and C5-TunePhos.

The catalysts may be pre-formed. In other words, the catalysts may be formed and optionally isolated before being reacted with the substrate (compound B). Alternatively, the catalyst may be formed in situ. In other words, the catalyst may form at the same time as being reacted with the substrate (compound B) i.e., the catalyst is not isolated prior to the hydrogenation reaction, but is formed from its precursor ligands in the reaction pot. Suitable pre-cursors for forming the catalyst, either as a pre-formed catalyst or in situ, are [Ru(p-cymene)Cl$_2$]$_2$, [Ru(benzene)Cl$_2$]Cl$_2$ and Ru(COD)(2-methylallyl)$_2$. A particularly suitable situ-formed catalyst may be prepared from [Ru(p-cymene)Cl$_2$]$_2$ and the C3-TunePhos ligand. Preferably, the catalyst is pre-formed.

In an embodiment, the hydrogenation is carried out in the presence of an acid. Optionally, the acid is H$_3$PO$_4$, CF$_3$CO$_2$H or HOAc. H$_3$PO$_4$ and CF$_3$CO$_2$H are preferred acid Preferably, the acid is H$_3$PO$_4$.

In an embodiment, the acid is present in a solvent. For example, the acid solvent is water. Suitably, a solution of 85% H₃PO₄ in water is used.

In an embodiment, the compound B/acid molar ratio ranges from 2/1 to 70/1. Suitably, the compound B/acid molar ratio ranges from 4/1 to 63/1. The preferred compound B/acid molar ratios are 4/1 and 25/1. Preferably, the compound B/acid molar ratio is 4/1.

In another embodiment, the compound B/catalyst molar ratio ranges from 100/1 to 4000/1. Suitably, the compound B/catalyst molar ratio ranges from 100/1 to 3000/1. Preferably, the compound B/catalyst molar ratio ranges from 100/1 to 2000/1. More preferably, the compound B/catalyst molar ratio ranges from 100/1 to 1000/1. Still more, preferably the compound B/catalyst molar ratio ranges from 100/1 to 250/1. Most preferably, the compound B/catalyst molar ratio is 250/1.

The hydrogenation may be carried out in the presence of a solvent. For example, the hydrogenation solvent is selected from a substituted or unsubstituted straight- or branched-chain C1 o C6 alcohol, an arene or mixtures thereof. Optionally, the solvent is selected from MeOH, dichloroethane (DCE), CF₃CH₂OH, MePh, tetrahydrofuran (THF) or EtOAc. Preferably, the solvent is methanol.

The hydrogenation may be carried out at a temperature ranging from 40° C. to 100° C. Suitably, the hydrogenation is carried out at a temperature ranging from 40° C. to 80° C. Preferably, the hydrogenation is carried out at a temperature ranging from 50° C. to 60° C. More preferably, the hydrogenation is carried out at a temperature of 60° C. When R₄ of compound B is t-butyl, the preferred temperature is lower than 80° C.

The hydrogenation may be carried out at a pressure ranging from 10 bars to 70 bars. Suitably, the hydrogenation is carried out at a pressure ranging from 20 bars to 60 bars. Preferably, the hydrogenation is carried out at a pressure ranging from 20 bars to 40 bars. Most preferably, the hydrogenation is carried out at a pressure of 30 bars.

In a further embodiment, the process further comprises subsequently recrystallising the compound of formula A. Optionally, the recrystallisation is carried out in DCM/hexane.

In an embodiment, compound A is in the form of the S enantiomer. In an alternative embodiment, compound A is in the form of the R enantiomer.

According to another aspect of the present invention, there is provided a process for preparing the S or R enantiomer of a compound of formula A,

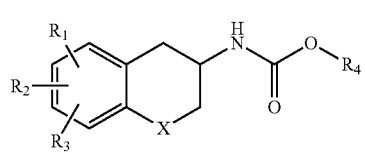

the process comprising subjecting a compound of formula B to asymmetric hydrogenation in the presence of a chiral transition metal catalyst and a source of hydrogen,

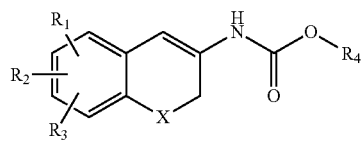

wherein X is CH₂, oxygen or sulphur; R₁, R₂ and R₃ are the same or different and signify hydrogens, halogens, alkyl, alkyloxy, hydroxy, nitro, alkylcarbonylamino, alkylamino, or dialkylamino group; and R₄ is alkyl or aryl, wherein the transition metal catalyst comprises a DiPh-MeO-BIPHEP ligand having the formula J,

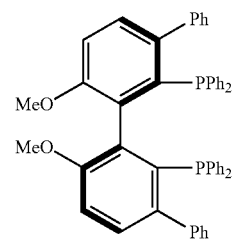

wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen, or nitro group; the term Ph represents a phenyl group; and the term halogen means fluorine, chlorine, bromine, or iodine.

Compound B may be referred to as an ene-carbamate.

In an embodiment, X is O. In another embodiment, at least one of R₁, R₂ and R₃ is fluorine.

Suitably, compound A has the following formula:

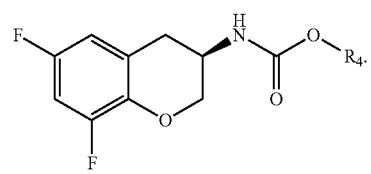

In an embodiment, R₄ is C₁ to C₄ alkyl. Optionally, R₄ is methyl (i.e., the methyl-substituted carbamate), ethyl (i.e., the ethyl-substituted carbamate) or ᵗBu (i.e., the ᵗBu-substituted carbamate). Preferably, R₄ is methyl. In an alternative embodiment, R₄ is benzyl (i.e., the benzyl-substituted carbamate).

In an embodiment, the catalyst is a rhodium-based catalyst. Suitably, the catalyst has the formula Rh(L")₂X/P*, wherein P* is the DiPh-MeO-BIPHEP ligand, L" is a diene such as norbornadiene (NBD) or cyclooctadiene (COD) and X is a counterion such as BF₄ or PF₆.

The catalysts may be pre-formed. In other words, the catalysts may be formed and optionally isolated before being reacted with the substrate (compound B). Alternatively, the catalyst may be formed in situ. In other words, the catalyst may form at the same time as with the hydrogenation reaction with the substrate (compound B). A suitable pre-cursor for forming the catalyst, either as a pre-formed catalyst or in situ, is Rh(NBD)₂PF₆.

In another embodiment, the compound B/catalyst molar ratio ranges from 50/1 to 4000/1. Suitably, the compound B/catalyst molar ratio ranges from 100/1 to 4000/1. Preferably, the compound B/catalyst molar ratio ranges from 100/1 to 3000/1. More preferably, the compound B/catalyst molar ratio ranges from 100/1 to 2000/1. More preferably still, the compound B/catalyst molar ratio ranges from 100/1 to 1000/1. Still more preferably, the compound B/catalyst molar ratio ranges from 100/1 to 250/1. Most preferably, the compound B/catalyst molar ratio is 100/1.

The hydrogenation may be carried out in the presence of a solvent. For example, the hydrogenation solvent is $CH_2Cl_2$ or PhMe, preferably $CH_2Cl_2$.

The hydrogenation may be carried out at a temperature ranging from 20° C. to 100° C. Suitably, the hydrogenation is carried out at a temperature ranging from 30° C. to 80° C. Preferably, the hydrogenation is carried out at a temperature ranging from 50° C. to 60° C. More preferably, the hydrogenation is carried out at a temperature of 60° C.

The hydrogenation may be carried out at a pressure ranging from 10 bars to 70 bars. Suitably, the hydrogenation is carried out at a pressure ranging from 20 bars to 60 bars. Preferably, the hydrogenation is carried out at a pressure ranging from 20 bars to 40 bars. Most preferably, the hydrogenation is carried out at a pressure of 30 bars.

In a further embodiment, the process further comprises subsequently recrystallising the compound of formula A. Optionally, the recrystallisation is carried out in DCM/hexane.

In an embodiment, compound A is in the form of the S enantiomer. In an alternative embodiment, compound A is in the form of the R enantiomer.

Compound B may be prepared, for example, by the process described in *Tetrahedron: Asymmetry* 10 (1999) 3467-3471.

According to another aspect of the present invention, there is provided a process for preparing the R or S enantiomer of a compound of formula C or salt thereof,

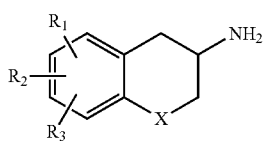

C wherein X is $CH_2$, oxygen or sulphur; and $R_1$, $R_2$, $R_3$ are each selected from hydrogen, halogen, alkyl, alkyloxy, hydroxyl, nitro, amino, alkylcarbonylamino, alkylamino, or dialkylamino, comprising forming the R or S enantiomer of a compound of formula A by a process as described above, followed by converting the R or S enantiomer of the compound A to the respective R or S enantiomer of a compound of formula C.

The compound A may be converted to compound C by a reaction involving substituting the group —C(=O)—O—$R_4$ with H.

The R or S enantiomer of compound A may be converted to the respective R or S enantiomer of the compound of formula C by hydrolysis.

According to another aspect of the present invention, there is provided a process for forming the R or S enantiomer of a compound of formula E or a salt thereof:

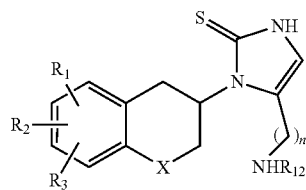

E wherein X is $CH_2$, oxygen or sulphur; and $R_1$, $R_2$, $R_3$ are each selected from hydrogen, halogen, alkyl, alkyloxy, hydroxyl, nitro, amino, alkylcarbonylamino, alkylamino, or dialkylamino, and $R_{12}$ is selected from hydrogen, alkyl or alkylaryl, comprising forming the R or S enantiomer of a compound of formula C according to the process described above, and converting the R or S enantiomer of the compound of formula C to the R or S enantiomer of the compound of formula E.

In an embodiment, X is oxygen. In another embodiment, at least one of $R_1$, $R_2$ and $R_3$ is fluorine.

In an embodiment, compound C is converted to compound E by using compound C as an amino component to build the N(1) moiety of the substituted imidazole-2-thione ring of compound E.

The amino group on the compound C may be converted to a 5-substituted imidazole-2-thione group, and the 5-substituted group is replaced with the group —$(CH_2)_n$—$NHR_{12}$, wherein $R_{12}$ signifies hydrogen, alkyl or alkylaryl group.

To form compound E, the R or S enantiomer of the compound of formula C may be reacted with a compound of formula D2

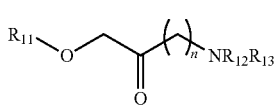

D2 where n signifies 1, 2 or 3; when n is 1 or 2, $R_{12}$ signifies hydrogen, alkyl, or alkylaryl group, $R_{11}$ signifies a hydroxyl protecting group and $R_{13}$ signifies an amino protecting group; when n signifies 3, $R_{11}$ signifies a hydroxyl protecting group but $R_{12}$ and $R_{13}$ taken together represent a phthalimido group; and with a water soluble thiocyanate salt in the presence of an organic acid in a substantially inert solvent, followed by subsequent deprotection of the intermediate products F to I:

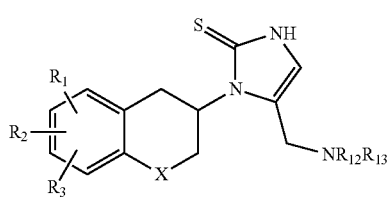

F

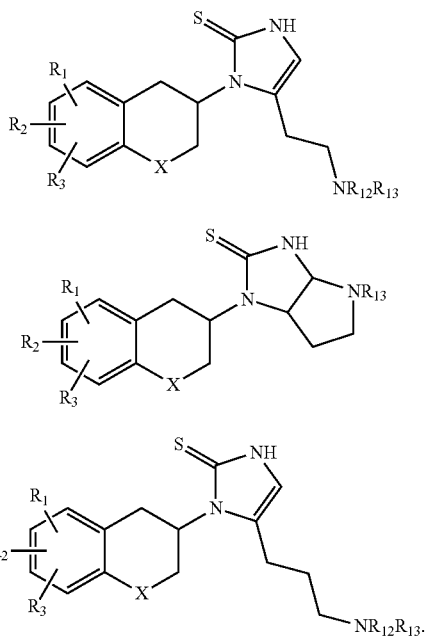

In an embodiment, X is O. In another embodiment, n is 2 or 3. Suitably, X is O and n is 2. Alternatively, X is O and n is 3. Optionally, at least one of $R_1$, $R_2$ and $R_3$ is halogen, preferably fluorine.

In an embodiment, the compound E is (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione, or a salt thereof. The salt is preferably the hydrochloride salt.

In an embodiment, the compound E is the respective R or S enantiomer of the compound of formula P:

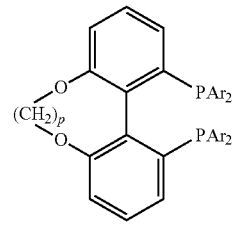

According to another aspect of the present invention, there is provided the use of a chiral catalyst comprising a transition metal complex comprising a chiral TunePhos ligand having the formula,

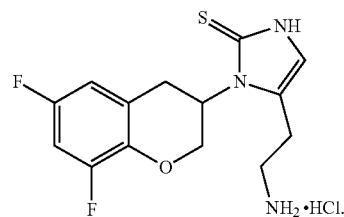

wherein p is an integer from 1 to 6, and Ar means aryl group in the asymmetric hydrogenation of a compound of formula B,

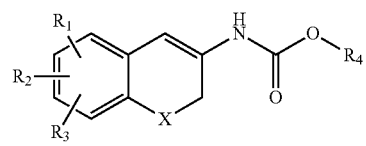

wherein compound B is as described above and the TunePhos ligand is as described above.

According to another aspect of the present invention, there is provided [Ru(p-cymene)(TunePhos)Cl]Cl, [Ru(TunePhos)Cl]$_2$(μ-Cl)$_3$(Me$_2$NH$_2$), [Ru(TunePhos)Cl]$_2$(μ-Cl)$_3$(Et$_2$NH$_2$), Ru(TunePhos)(BF$_4$)$_2$, Ru(TunePhos)(OAc)$_2$, Ru(TunePhos)(acac)$_2$, Ru(TunePhos)(CF$_3$COO)$_2$ and Ru(Tune Phos)Cl$_2$(dmf)$_m$ wherein m is 2, 3, or 4. Preferred catalysts are Ru(TunePhos)(acac)$_2$ and Ru(TunePhos)(CF$_3$COO)$_2$. Preferred TunePhos ligands for inclusion in the catalysts are C3-, C4-, and C5-TunePhos.

According to a further aspect of the present invention, there is provided a catalyst system comprising a ruthenium-based transition metal complex and an acid additive, wherein the complex comprises a TunePhos ligand as described above. Optionally, the acid is $H_3PO_4$, $CF_3CO_2H$ or HOAc. $H_3PO_4$ and $CF_3CO_2H$ are preferred acids. Preferably, the acid is $H_3PO_4$.

Ru-catalysed hydrogenation investigations have revealed that full conversion and e.e's more than 90% were obtained using the methyl-substituted ene-carbamate in the presence of ruthenium-TunePhos-based catalysts.

The reactivity and enantioselectivity in the asymmetric hydrogenation of the ene-carbamate substrates has been found to vary in the order OBn<O$^t$Bu<OMe.

The methyl-substituted ene-carbamate exhibited similar conversions and e.e.'s to the $^t$Bu-substituted ene-carbamate, although reaction of the $^t$Bu-substituted ene-carbamate was sometimes found to result in by-products.

Particularly, effective combinations of ligands, acid additives, and reaction conditions include:

[Ru(C4-TunePhos)(acac)$_2$] with $H_3PO_4$ acid additive. The reaction conditions are preferably 60° C., 30 bar hydrogen, substrate/catalyst 250/1 and/or acid/catalyst 63/1.

[Ru(C5-TunePhos)(acac)$_2$] with $H_3PO_4$ acid additive. The reaction conditions are preferably 60° C., 30 bar hydrogen, substrate/catalyst 250/1 and/or acid/catalyst 63/1.

[Ru(C5-TunePhos)(CF$_3$COO)$_2$] with $H_3PO_4$ acid additive. The reaction conditions are preferably 60° C., 30 bar hydrogen, substrate/catalyst 250/1 and/or acid/catalyst 63/1.

[Ru(C3-TunePhos)(CF$_3$COO)$_2$]. The reaction conditions are preferably 60° C., 30 bar hydrogen, and/or substrate/catalyst 250/1. The presence of $H_3PO_4$ as acid additive is also beneficial, with an acid/catalyst ratio of 63/1 being preferred.

[Ru(C3-TunePhos)(acac)$_2$] with $H_3PO_4$ acid additive. The reaction conditions are preferably 40° C., 30 bar hydrogen, substrate/catalyst 250/1 and/or acid/catalyst 63/1. Alternatively, the reaction conditions may be 30 bar hydrogen, substrate/catalyst 3000/1 and/or acid/catalyst 750/1.

Preferred features, embodiments and reaction conditions of each aspect of the invention are as for each of the other aspects mutatis mutandis unless the context demands otherwise.

EXAMPLES

An investigation of the effect of the catalyst on the enantioselective hydrogenation of the prochiral ene-carbamates la-c (as shown in Scheme 1 below) was carried out using ruthenium-TunePhos-based catalysts (Tables 1 to 29) and rhodium-DiPh-MeO-BIPHEP-based catalysts (Tables 30 to 32).

Scheme 1

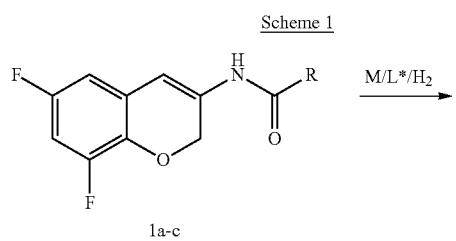

1a-c

-continued

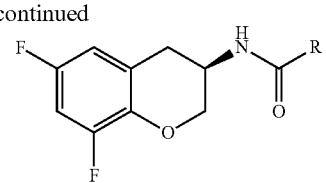

2a-c

R = a: OMe b: O$^t$Bu c: OBn

General Procedure for Asymmetric Hydrogenation

A 300 mL-volume autoclave with glass vial (20 mL) was charged with substrate, catalyst as well as oxygen-free solvent under nitrogen. This autoclave was charged with hydrogen to the desired pressure and stirred at room temperature or heated with oil bath. After hydrogen was released carefully, the reaction mixture was diluted and used as HPLC sample. As far as hydrogenation of 1b, the reaction mixture was concentrated and $^1$H NMR checked to determine conversion.

Analytical Method

The enantiomeric excess (e.e.) was determined using HPLC and the following conditions:

HPLC: Agilent 1100 series
Column: Chiralpak AD-H, 25 cm
Mobile Phase: MeOH/IPA=70/30
Flow Rare: 0.5 mL/min
Detection: UV@210 and 254 nm
Retention Time of 1a: 11.7 min
Retention Time of R-2a: 8.8 min
Retention Time of S-2a: 10.6 min
Retention Time of 1b: 8.4 min
Retention Time of R-2b: 8.3 min
Retention Time of S-2b: 9.2 min
Retention Time of 1c: 15.8 min
Retention Time of R-2c: 12.0 min
Retention Time of S-2c: 14.4 min The conversion ("Conv") was determined by:
HPLC area for substrates 1a and 1c.
$^1$H NMR of crude reaction mixture for substrate 1b.

The chemical purity was determined by:
HPLC: HP 1050 series
Column: Apollo C18 5u, 25 cm
Mobile Phase: H$_2$O (0.05% TFA)/CH$_3$CN (0.05% TFA) =50/50
Flow Rare: 1.0 mL/min
Detection: UV@210 nm
Retention Time of R-2a: 8.6 min Ruthenium—TunePhos Catalysis Initial Tests Initial tests were carried out on the 1a substrate using a C1 to C6-TunePhos-based catalyst and the results are shown in Table 1 below.

TABLE 1

Asymmetric Hydrogenation of 1a - Ligand Screening

| Catalyst | Conv (%) (254 nm) | Conv (%) (210 nm) | Ee (%) (210 nm) |
|---|---|---|---|
| [Ru(p-cymene)(S-C1-TunePhos)Cl]Cl | 92 | 98 | 82.1 (S) |
| [Ru(p-cymene)(S-C2-TunePhos)Cl]Cl | 90 | 97 | 89.6 (S) |
| [Ru(p-cymene)(S-C3-TunePhos)Cl]Cl | 78 | 94 | 88.8 (S) |
| [Ru(p-cymene)(S-C4-TunePhos)Cl]Cl | 98 | 98 | 90.7 (S) |
| [Ru(p-cymene)(S-C5-TunePhos)Cl]Cl | 97 | 99 | 91.3 (S) |
| [Ru(p-cymene)(S-C6-TunePhos)Cl]Cl | 98 | 99 | 90.6 (S) |

All reactions were carried out at 50° C. under initial hydrogen pressure of 60 bar in methanol for 17 hours. The ratio of sub/Ru was in the range of 70~100.

Solvent Effect

Solvent effect on the enantioselectivity of 1a using [Ru(p-cymene)(S—C3-TunePhos)Cl]Cl as catalyst was performed and the results are listed in Table 2.

TABLE 2

Asymmetric Hydrogenation of 1a - Solvent Effect

| Catalyst (mg) | Solvent | Conv (%) (254 nm) | Conv (%) 210 nm | Ee (%) 210 nm |
|---|---|---|---|---|
| [Ru(p-cymene)(S-C3-TunePhos)Cl]Cl | MeOH | 78 | 94 | 88.8 (S) |
| [Ru(p-cymene)(S-C3-TunePhos)Cl]Cl | DCE | 13 | 44 | 80.8 (S) |
| [Ru(p-cymene)(S-C3-TunePhos)Cl]Cl | $CF_3CH_2OH$ | 3 | 19 | 44.4 (S) |
| [Ru(p-cymene)(S-C3-TunePhos)Cl]Cl | MePh | 97 | >99 | 85.6 (S) |
| [Ru(p-cymene)(S-C3-TunePhos)Cl]Cl | THF | 76 | 95 | 83.1 (S) |
| [Ru(p-cymene)(S-C3-TunePhos)Cl]Cl | EtOAc | 79 | 96 | 82.9 (S) |

All reactions were carried out at 50~60° C. under initial hydrogen pressure of 60 bar for 17~18 hrs. The ratio of sub/Ru was in the range of 90~120.

Ligand Effect

Various C3-TunePhos/ruthenium species and C4-TunePhos/ruthenium species were tested and the results are shown in Table 3.

TABLE 3

Asymmetric Hydrogenation of 1a - Catalyst Species Screening

| Catalyst (mg) | Sub/Cat | Conv (%) (254 nm) | Conv (%) (210 nm) | Ee (%) (210 nm) |
|---|---|---|---|---|
| [Ru(p-cymene)(S-C3-TunePhos)Cl]Cl | 94 | 78 | 94 | 88.8 (S) |
| [Ru(S-C3-TunePhos)Cl]$_2$(μ-Cl)$_3$(Me$_2$NH$_2$) | 60 | 96 | 99 | 90.0 (S) |
| Ru(S-C3-TunePhos)(BF$_4$)$_2$ | 67 | 97 | 99 | 86.8 (S) |
| Ru(S-C3-TunePhos)(OAc)$_2$ | 121 | 95 | 98 | 88.4 (S) |
| Ru(S-C3-TunePhos)(CF$_3$COO)$_2$ | 135 | >99 | >99 | 91.8 (S) |
| Ru(S-C3-TunePhos)Cl$_2$(dmf)$_m$ | 120 | >99 | >99 | 88.2 (S) |
| [Ru(p-cymene)(S-C4-TunePhos)Cl]Cl | 79 | 97 | 98 | 90.7 (S) |
| [Ru(S-C4-TunePhos)Cl]$_2$(μ-Cl)$_3$(Me$_2$NH$_2$) | 116 | >99 | >99 | 88.7 (S) |
| [Ru(S-C4-TunePhos)Cl]$_2$(μ-Cl)$_3$(Et$_2$NH$_2$) | 109 | >99 | >99 | 90.5 (S) |

All reactions were carried out at 50~60° C. under initial hydrogen pressure of 60 bar for 17~18 hrs.

In Situ Catalysis

Using [Ru(p-cymene)Cl$_2$]$_2$ as precursor, the enantioselectivity of in situ-formed catalysts was tested (Table 4).

Initial results showed that there was not much difference in enantioselectivity between a preformed catalyst and an in situ-formed catalyst of [Ru(p-cymene)Cl$_2$]Cl$_2$ combined with C3-TunePhos as ligand.

The reactions were very slow using in situ formed catalysts.

When the other precursors, i.e., [Ru(benzene)Cl$_2$]Cl$_2$ and Ru(COD)(2-methylallyl)$_2$, were employed instead of [Ru(p-cymene)Cl$_2$]Cl$_2$ similar results were obtained (Tables 5 and 6).

Addition of an acid enhanced the reactivity (Table 7).

TABLE 4

Asymmetric Hydrogenation of 1a - Catalyzed by In Situ Catalysts with [Ru(p-cymene)Cl$_2$]$_2$

| Catalyst (mg) | Sub (mg) | Conv (%) (254 nm) | Conv (%) (210 nm) | Ee (%) (210 nm) |
|---|---|---|---|---|
| [Ru(p-cymene)(R-C3-TunePhos)Cl]Cl, 6.0 mg | 55 | 95 | 99 | 88.4 (R) |
| [Ru(p-cymene)Cl$_2$]$_2$, 3.0 mg R-C3-TunePhos, 2.0 mg | 50 | 94 | 98 | 88.3 (R) |

All reactions were carried out at 60° C. under initial hydrogen pressure of 30 bar for 18 hrs.

TABLE 5

Asymmetric Hydrogenation of 1a - Catalyzed by in Situ Catalysts with [Ru(benzene)Cl$_2$]$_2$

| Catalyst (mg) | Sub (mg) | Conv (%) 254 nm | Conv (%) 210 nm | Ee (%) 210 nm |
|---|---|---|---|---|
| [Ru(benzene)Cl$_2$]$_2$, 2.5 mg R-C3-TunePhos, 6.5 mg | 55 | 50 | 84 | 88.4 (R) |

All reactions were carried out at 60° C. under initial hydrogen pressure of 30 bar for 18 hrs.

TABLE 6

Asymmetric Hydrogenation of 1a - Catalyzed by in Situ Catalysts with Ru(COD)(2-methylallyl)$_2$

| Catalyst (mg) | Sub (mg) | Conv (%) 254 nm | Conv (%) 210 nm | Ee (%) 210 nm |
|---|---|---|---|---|
| Ru(COD)(2-methylallyl)$_2$, 3.1 mg R-C3-TunePhos, 6.0 mg | 65 | 11 | 39 | 63.3 (R) |

All reactions were carried out at 60° C. under initial hydrogen pressure of 30 bar for 18 hrs.

TABLE 7

Asymmetric Hydrogenation of 1a - Effect of Acid Additive

| Catalyst | Acid Acid/C | Conv (%) (254 nm) | Conv (%) (210 nm) | Ee (%) (210 nm) |
|---|---|---|---|---|
| [Ru(p-cymene)Cl$_2$]/R-C3-TunePhos | — | <40 | 61 | 84.4 (R) |
| [Ru(p-cymene)Cl$_2$]/R-C3-TunePhos | $H_3PO_4$ 25/1 | 95 | 99 | 90.1 (R) |
| [Ru(benzene)Cl$_2$]/R-C3-TunePhos | — | 87 | 97 | 85.3 (R) |
| [Ru(benzene)Cl$_2$]/R-C3-TunePhos | $H_3PO_4$ 25/1 | 77 | 94 | 73.7 (R) |
| Ru(COD)(methylallyl)$_2$/R-C3-TunePhos | — | 7 | 30 | 20.3 (R) |
| Ru(COD)(methylallyl)$_2$/R-C3-TunePhos | $H_3PO_4$ 25/1 | 45 | 81 | 68.8 (R) |

All reactions were carried out at 60° C. under 30 bar of hydrogen for 20 hrs using 0.3 mmol substrate in 3 mL of methanol. The ratio of sub/Ru was 100.

Similar reaction conditions were used on Cp-TunePhos in situ-formed catalysts at S/C of 250 (Table 8).

TABLE 8

Asymmetric Hydrogenation of 1a Catalyzed by in situ [Ru(p-cymene)Cl$_2$]$_2$/Cp-TunePhos

| Catalyst (mg) | Sub (mg) | S/Ru | Acid Acid/C | [S] mmol/mL | Conv (%) (254 nm) | Conv (%) (210 nm) | Ee (%) (210 nm) |
|---|---|---|---|---|---|---|---|
| [Ru(p-cymene)Cl$_2$]$_2$/ R-C2-TunePhos 0.36 mg/0.7 mg | 1a 73 | 250 | H$_3$PO$_4$ 25/1 | 0.1 | <5 | <5 | — |
| [Ru(p-cymene)Cl$_2$]$_2$/ R-C3-TunePhos 0.36 mg/0.7 mg | 1a 73 | 250 | H$_3$PO$_4$ 25/1 | 0.1 | <5 | <5 | — |
| [Ru(p-cymene)Cl$_2$]$_2$/ S-C4-TunePhos 0.36 mg/0.8 mg | 1a 73 | 250 | H$_3$PO$_4$ 25/1 | 0.1 | <5 | <5 | — |
| [Ru(p-cymene)Cl$_2$]$_2$/ S-C5-TunePhos 0.36 mg/0.8 mg | 1a 73 | 250 | H$_3$PO$_4$ 25/1 | 0.1 | <5 | 5 | — |
| [Ru(p-cymene)Cl$_2$]$_2$/ S-C6-TunePhos 0.36 mg/0.8 mg | 1a 73 | 250 | H$_3$PO$_4$ 25/1 | 0.1 | 63 | 89 | 91.0 (S) |

All reactions were carried out at 60° C. under 30 bar of hydrogen for 20 hrs.

Higher acid amounts increased activity (Table 9).

TABLE 9

Asymmetric Hydrogenation of 1a Catalyzed by in situ [Ru(p-cymene)Cl$_2$]$_2$/Cp-TunePhos

| Catalyst (mg) | Sub (mg) | S/Ru | Acid Acid/C | [S] mmol/mL | Conv (%) (254 nm) | Conv (%) (210 nm) | Ee (%) (210 nm) |
|---|---|---|---|---|---|---|---|
| [Ru(p-cymene)Cl$_2$]$_2$/ R-C2-TunePhos 0.36 mg/0.7 mg | 1a 73 | 250 | H$_3$PO$_4$ 63/1 | 0.1 | 96 | >99 | 52.2 (R) |
| [Ru(p-cymene)Cl$_2$]$_2$/ R-C3-TunePhos 0.36 mg/0.7 mg | 1a 73 | 250 | H$_3$PO$_4$ 63/1 | 0.1 | 7 | 29 | 86.9 (R) |
| [Ru(p-cymene)Cl$_2$]$_2$/ S-C4-TunePhos 0.36 mg/0.8 mg | 1a 73 | 250 | H$_3$PO$_4$ 63/1 | 0.1 | 98 | >99 | 89.9 (S) |
| [Ru(p-cymene)Cl$_2$]$_2$/ S-C5-TunePhos 0.36 mg/0.8 mg | 1a 73 | 250 | H$_3$PO$_4$ 63/1 | 0.1 | <5 | 10 | 69.6 (S) |
| [Ru(p-cymene)Cl$_2$]$_2$/ S-C6-TunePhos 0.36 mg/0.8 mg | 1a 73 | 250 | H$_3$PO$_4$ 63/1 | 0.1 | 99 | >99 | 90.4 (S) |

All reactions were carried out at 60° C. under 30 bar of hydrogen for 20 hrs.

Acid Effect

Ru(R—C3-TunePhos)(acac)$_2$ was tested (Table 10). Acid additives, particularly H$_3$PO$_4$ and CF$_3$COOH, increased conversion.

TABLE 10

Asymmetric Hydrogenation of 1a-c-Catalyzed by Ru(R-C3-TunePhos)(acac)$_2$ with Acid Additive

| Substrate | Acid Acid/C | Conv (%) (254 nm) | Conv (%) (210 nm) | Ee (%) (210 nm) |
|---|---|---|---|---|
| 1a | — | <5 | <5 | — |
| 1a | H$_3$PO$_4$ 25/1 | >99 | >99 | 91.7 (R) |
| 1a | CF$_3$CO$_2$H 25/1 | >99 | >99 | 91.4 (R) |
| 1a | HOAc 25/1 | 90 | 98 | 90.0 (R) |
| 1b | H$_3$PO$_4$ 25/1 | >99 $^1$H NMR | — | 86.3 (R) |
| 1c | H$_3$PO$_4$ 25/1 | 38 | 75 | 89.9 (R) |

All reactions were carried out at 60° C. under 30 bar of hydrogen for 20 hrs using 0.3 mmol substrate in 3 mL of methanol. The ratio of sub/Ru was 100.

As can be seen from Table 10, the hydrogenation of substrate 1b using Ru(R—C3-TunePhos)(acac)$_2$ provided complete conversion and about 86% ee under the standard conditions. Not much difference in activity was observed between 1a and 1b.

Regarding the substrate 1c, asymmetric hydrogenation was always slower than 1a and 1b under standard conditions, but the e.e. was similar to that obtained for the other two substrates 1a and 1b.

The results in Table 10 showed that addition of acid increased the activity significantly, so the acid effect on other types of precursor was tested (Table 11).

TABLE 11

Asymmetric Hydrogenation of 1a - Effect of Acid Additive

| Catalyst (mg) | Sub (mg) | TON | Acid (mg) Acid/C | Conv (%) (254 nm) | Conv (%) (210 nm) | Ee (%) (210 nm) |
|---|---|---|---|---|---|---|
| [Ru(R-C3-TunePhos)(p-cymene)Cl]Cl 2.7 mg | 73 | 100 | — | 92 | 98 | 90.1 (R) |
| [Ru(R-C3-TunePhos)(p-cymene)Cl]Cl 2.7 mg | 73 | 100 | $H_3PO_4$ 8.7 25/1 | 92 | 98 | 90.0 (R) |
| [Ru(p-cymene)Cl]$_2$/R-C3-TunePhos 0.9 mg/1.8 mg | 71 | 100 | — | <40 | 61 | 84.4 (R) |
| [Ru(p-cymene)Cl]$_2$/R-C3-TunePhos 0.9 mg/1.9 mg | 73 | 102 | $H_3PO_4$ 8.5 25/1 | 95 | 99 | 90.1 (R) |
| [Ru(benzene)Cl]$_2$/R-C3-TunePhos 0.7 mg/1.7 mg | 72 | 106 | — | 87 | 97 | 85.3 (R) |
| [Ru(benzene)Cl]$_2$/R-C3-TunePhos 0.8 mg/2.0 mg | 78 | 101 | $H_3PO_4$ 9.2 25/1 | 77 | 94 | 73.7 (R) |
| Ru(COD)(methylallyl)$_2$/R-C3-TunePhos 0.9 mg/1.8 mg | 73 | 107 | — | 8 | 30 | 27.8 (R) |
| Ru(COD)(methylallyl)$_2$/R-C3-TunePhos 0.9 mg/1.9 mg | 72 | 106 | — | 7 | 30 | 20.3 (R) |
| Ru(COD)(methylallyl)$_2$/R-C3-TunePhos 0.9 mg/2.0 mg | 71 | 104 | $H_3PO_4$ 8.2 25/1 | 45 | 81 | 68.8 (R) |

All reactions were carried out at 60° C. under 30 bar of hydrogen for 20 hrs using 0.1 mmol substrate in 3 mL of methanol.

The effect of the acid was tested at a higher temperature of 80° C. (Table 12).

TABLE 12

Asymmetric Hydrogenation of 1a-c - Catalyzed by Ru(R-C3-TunePhos)(acac)$_2$ - 80° C.

| Catalyst (mg) | Sub (mg) | S/Ru | $H_3PO_4$ (mg) Acid/C | [S] mmol/mL | Conv (%) (254 nm) | Conv (%) (210 nm) | Ee (%) (210 nm) |
|---|---|---|---|---|---|---|---|
| Ru(R-C3-TunePhos)(acac)$_2$, 2.7 mg | 1a 73 | 100 | 9.3 25/1 | 0.1 | >99 | >99 | 90.8 (R) |
| Ru(R-C3-TunePhos)(acac)$_2$, 2.7 mg | 1b 86 | 100 | 9.3 25/1 | 0.1 | >99 $^1$H NMR | — | 88.9 (R) |
| Ru(R-C3-TunePhos)(acac)$_2$, 2.7 mg | 1c 97 | 101 | 9.3 25/1 | 0.1 | 90 | 97 | 85.5 (R) |

All reactions were carried out at 80° C. under 30 bar of hydrogen for 20 hrs.

The reactions in Table 12 were conducted using a preformed catalyst. The reactions were repeated with in situ formation of the catalyst (Table 13).

TABLE 13

Asymmetric Hydrogenation of 1a-c Catalyzed by in situ [Ru(p-cymene)Cl₂]₂/R-C3-TunePhos- 80° C.

| Catalyst (mg) | Sub (mg) | S/Ru | H₃PO₄ (mg) Acid/C | [S] mmol/mL | Conv (%) (254 nm) | Conv (%) (210 nm) | Ee (%) (210 nm) |
|---|---|---|---|---|---|---|---|
| [Ru(p-cymene)Cl₂]₂/ R-C3-TunePhos 0.9 mg/1.8 mg | 1a 73 | 102 | 8.5 25/1 | 0.1 | 99 | >99 | 87.9 (R) |
| [Ru(p-cymene)Cl₂]₂/ R-C3-TunePhos 0.9 mg/1.8 mg | 1b 86 | 103 | 8.5 25/1 | 0.1 | >99 | — | 84.3 (R) |
| [Ru(p-cymene)Cl₂]₂/ R-C3-TunePhos 0.9 mg/1.8 mg | 1c 96 | 103 | 8.5 25/1 | 0.1 | 62 | 89 | 83.1 (R) |

All reactions were carried out at 80° C. under 30 bar of hydrogen for 20 hrs.

The effect of (CF₃COO)₂ on C3, C4 and C5-TunePhos combined with (acac)₂ was tested on substrates 1a, 1b and 1c (Tables 14, 15 and 16, respectively).

TABLE 14

Asymmetric Hydrogenation of 1a

| Catalyst (mg) | Sub (mg) | Acid Acid/C | [S] mmol/mL | Conv (%) (254 nm) | Conv (%) (210 nm) | Ee (%) (210 nm) |
|---|---|---|---|---|---|---|
| Ru(R-C3-TunePhos) (acac)₂, 1.1 mg | 1a 75 | H₃PO₄ 63/1 | 0.1 | >99 | >99 | 91.4 (R) |
| Ru(R-C3-TunePhos) (CF₃COO)₂, 1.1 mg | 1a 73 | — | 0.1 | >99 | >99 | 89.0 (R) |
| Ru(R-C4-TunePhos) (CF₃COO)₂, 1.1 mg | 1a 76 | — | 0.1 | >99 | >99 | 91.7 (R) |
| Ru(S-C4-TunePhos) (acac)₂, 0.7 mg | 1a 47 | H₃PO₄ 63/1 | 0.1 | >99 | >99 | 91.7 (S) |
| Ru(S-C5-TunePhos) (acac)₂, 0.7 mg | 1a 46 | H₃PO₄ 63/1 | 0.1 | >99 | >99 | 92.0 (S) |
| Ru(S-C5-TunePhos) (CF₃COO)₂, 0.7 mg | 1a 45 | — | 0.1 | >99 | >99 | 92.5 (S) |

All reactions were carried out at 60° C. under 30 bar of hydrogen for 20 hrs at S/C of 250.

TABLE 15

Asymmetric Hydrogenation of 1b

| Catalyst (mg) | Sub (mg) | Acid Acid/C | [S] mmol/mL | Conv (%) ¹H NMR | Ee (%) (210 nm) |
|---|---|---|---|---|---|
| Ru(R-C3-TunePhos) (acac)₂, 0.7 mg | 1b 56 | H₃PO₄ 63/1 | 0.1 | >99 | 89.9 (R) |
| Ru(R-C3-TunePhos) (CF₃COO)₂, 0.7 mg | 1b 54 | — | 0.1 | >99 | 90.8 (R) |
| Ru(R-C4-TunePhos) (CF₃COO)₂, 0.7 mg | 1b 54 | — | 0.1 | >99 | 90.8 (R) |
| Ru(S-C4-TunePhos) (acac)₂, 0.7 mg | 1b 55 | H₃PO₄ 63/1 | 0.1 | >99 | 94.8 (S) |
| Ru(S-C5-TunePhos) (acac)₂, 0.7 mg | 1b 54 | H₃PO₄ 63/1 | 0.1 | >99 | 92.8 (S) |
| Ru(S-C5-TunePhos) (CF₃COO)₂, 0.7 mg | 1b 53 | — | 0.1 | >99 | 91.5 (S) |

All reactions were carried out at 60° C. under 30 bar of hydrogen for 20 hrs at S/C of 250.

TABLE 16

Asymmetric Hydrogenation of 1c

| Catalyst (mg) | Sub (mg) | Acid Acid/C | [S] mmol/mL | Conv (%) (254 nm) | Conv (%) (210 nm) | Ee (%) (210 nm) |
|---|---|---|---|---|---|---|
| Ru(R-C3-TunePhos) (acac)₂, 0.7 mg | 1c 62 | H₃PO₄ 63/1 | 0.1 | 12 | 42 | 89.6 (R) |
| Ru(R-C3-TunePhos) (CF₃COO)₂, 0.7 mg | 1c 60 | — | 0.1 | 10 | 35 | 90.0 (R) |
| Ru(R-C4-TunePhos) (CF₃COO)₂, 0.7 mg | 1c 60 | — | 0.1 | 5 | 20 | 88.3 (R) |

TABLE 16-continued

Asymmetric Hydrogenation of 1c

| Catalyst (mg) | Sub (mg) | Acid Acid/C | [S] mmol/mL | Conv (%) (254 nm) | Conv (%) (210 nm) | Ee (%) (210 nm) |
|---|---|---|---|---|---|---|
| Ru(S-C4-TunePhos)(acac)$_2$, 0.7 mg | 1c 61 | H$_3$PO$_4$ 63/1 | 0.1 | 17 | 52 | 90.7 (S) |
| Ru(S-C5-TunePhos)(acac)$_2$, 0.7 mg | 1c 60 | H$_3$PO$_4$ 63/1 | 0.1 | 19 | 56 | 90.6 (S) |
| Ru(S-C5-TunePhos)(CF$_3$COO)$_2$, 0.7 mg | 1c 60 | — | 0.1 | 12 | 41 | 90.4 (S) |

All reactions were carried out at 60° C. under 30 bar of hydrogen for 20 hrs at S/C of 250.

Temperature Effect

The temperature effect experiments were carried out using two catalysts Ru(C3-TunePhos)(acac)$_2$ and Ru(C4-TunePhos)(acac)$_2$ (Table 17).

TABLE 17

Asymmetric Hydrogenation of 1a Catalyzed by Ru(C$_F$-TunePhos)(acac)$_2$ - Temperature Effect

| Catalyst | Sub/Ru | Acid (mg) Acid/C | Temp (° C.) | Conv (%) (254 nm) | Conv (%) (210 nm) | Ee (%) (210 nm) |
|---|---|---|---|---|---|---|
| Ru(R-C3-TunePhos)(acac)$_2$ | 250 | H$_3$PO$_4$ 63/1 | 40 | >99 | >99 | 91.7 (R) |
| Ru(R-C3-TunePhos)(acac)$_2$ | 250 | H$_3$PO$_4$ 63/1 | 60 | >99 | >99 | 91.4 (R) |
| Ru(R-C3-TunePhos)(acac)$_2$ | 250 | H$_3$PO$_4$ 63/1 | 80 | >99 | >99 | 91.0 (R) |
| Ru(R-C3-TunePhos)(acac)$_2$ | 250 | H$_3$PO$_4$ 63/1 | 100 | >99 | >99 | 90.1 (R) |
| Ru(S-C4-TunePhos)(acac)$_2$ | 250 | H$_3$PO$_4$ 63/1 | 40 | >99 | >99 | 92.3 (S) |
| Ru(S-C4-TunePhos)(acac)$_2$ | 250 | H$_3$PO$_4$ 63/1 | 60 | >99 | >99 | 91.7 (S) |
| Ru(S-C4-TunePhos)(acac)$_2$ | 250 | H$_3$PO$_4$ 63/1 | 80 | >99 | >99 | 91.7 (S) |
| Ru(S-C4-TunePhos)(acac)$_2$ | 250 | H$_3$PO$_4$ 63/1 | 100 | >99 | >99 | 91.4 (S) |

All reactions were carried out at 30 bar of hydrogen for 20 hrs using 0.3 mmol substrate in 3 mL of methanol.

The enantioselectivity was temperature independent in the range of 40 to 100° C.

When substrates 1b and 1c were tested under the same conditions, similar results were obtained (Tables 18 and 19).

Regarding substrate 1b, the enantioselectivity remained almost the same in the tested temperature range. However, there was always about 5% byproducts detected on the HPLC for the hydrogenation of 1b, especially at higher temperature (80-100° C.).

Regarding substrate 1c, e.e. dropped slightly at higher temperature.

TABLE 18

Asymmetric Hydrogenation of 1b

| Catalyst (mg) | Temp (° C.) | Conv (%) $^1$H NMR | Ee (%) 210 nm |
|---|---|---|---|
| Ru(R-C3-TunePhos)(acac)$_2$ | 40 | >99 | 89.5 (R) |
| Ru(R-C3-TunePhos)(acac)$_2$ | 60 | >99 | 89.9 (R) |
| Ru(R-C3-TunePhos)(acac)$_2$ | 80 | >99 | 89.7 (R) |
| Ru(R-C3-TunePhos)(acac)$_2$ | 100 | >99 | 89.5 (R) |

All reactions were carried out at 30 bar of hydrogen for 20 hrs using 0.2 mmol substrate in 2 mL of methanol. The ratio of sub/H$_3$PO$_4$/Ru=250/63/1.

TABLE 19

Asymmetric Hydrogenation of 1c

| Catalyst (mg) | Temp (° C.) | Conv (%) 254 nm | Conv (%) 210 nm | Ee (%) 210 nm |
|---|---|---|---|---|
| Ru(R-C3-TunePhos)(acac)$_2$ | 60 | 12 | 42 | 89.6 (R) |
| Ru(R-C3-TunePhos)(acac)$_2$ | 80 | 96 | 99 | 85.7 (R) |

All reactions were carried out at 30 bar of hydrogen for 20 hrs using 0.2 mmol substrate in 2 mL of methanol. The ratio of sub/$H_3PO_4$/Ru=250/63/1.

Further reactions were carried out at 80° C. (Tables 20, 21 and 22).

TABLE 20

Asymmetric Hydrogenation of 1a at 80° C.

| Catalyst (mg) | Sub (mg) | Acid Acid/C | [S] mmol/mL | Conv (%) (254 nm) | Conv (%) (210 nm) | Ee (%) (210 nm) |
|---|---|---|---|---|---|---|
| Ru(R-C3-TunePhos)(acac)$_2$, 0.7 mg | 1a 46 | $H_3PO_4$ 63/1 | 0.1 | >99 | >99 | 91.0 (R) |
| Ru(S-C4-TunePhos)(acac)$_2$, 0.7 mg | 1a 45 | $H_3PO_4$ 63/1 | 0.1 | >99 | >99 | 91.7 (S) |
| [Ru(p-cymene)Cl$_2$]$_2$/ S-C4-TunePhos 0.24 mg/0.5 mg | 1a 47 | $H_3PO_4$ 63/1 | 0.1 | <5 | 8 | ND |
| [Ru(p-cymene)Cl$_2$]$_2$/ S-C6-TunePhos 0.24 mg/0.5 mg | 1a 47 | $H_3PO_4$ 63/1 | 0.1 | <5 | 5 | ND |

All reactions were carried out at 30 bar of hydrogen for 20 hrs at 80° C. at a S/C of 250.

TABLE 21

Asymmetric Hydrogenation of 1b at 80° C.

| Catalyst (mg) | Sub (mg) | Acid Acid/C | $H_2$ (bar) | Time (h) | [S] mmol/mL | Conv (%) $^1$H NMR | Ee (%) (210 nm) |
|---|---|---|---|---|---|---|---|
| Ru(R-C3-TunePhos)(acac)$_2$, 0.7 mg | 1b 56 | $H_3PO_4$ 63/1 | 30 | 20 | 0.1 | >99 | 89.7 (R) |
| Ru(S-C4-TunePhos)(acac)$_2$, 0.7 mg | 1b 55 | $H_3PO_4$ 63/1 | 30 | 2 | 0.1 | >99 | 90.0 (S) |
| [Ru(p-cymene)Cl$_2$]$_2$/ S-C4-TunePhos, 0.24 mg/0.5 mg | 1b 56 | $H_3PO_4$ 63/1 | 30 | 20 | 0.1 | 18 | ND |
| [Ru(p-cymene)Cl$_2$]$_2$/ S-C6-TunePhos, 0.24 mg/0.5 mg | 1b 56 | $H_3PO_4$ 63/1 | 30 | 20 | 0.1 | <10 | ND |

All reactions were carried out at 30 bar of hydrogen at 80° C. at a S/C of 250.

HPLC on the Table 21 results showed ~5% unidentified byproducts.

TABLE 22

Asymmetric Hydrogenation of 1c at 80° C.

| Catalyst (mg) | Sub (mg) | Acid Acid/C | [S] mmol/mL | Conv (%) (254 nm) | Conv (%) (210 nm) | Ee (%) (210 nm) |
|---|---|---|---|---|---|---|
| Ru(R-C3-TunePhos)(acac)$_2$, 0.7 mg | 1c 62 | $H_3PO_4$ 63/1 | 0.1 | 96 | 99 | 85.7 (R) |
| Ru(S-C4-TunePhos)(acac)$_2$, 0.7 mg | 1c 61 | $H_3PO_4$ 63/1 | 0.1 | 89 | 98 | 87.6 (S) |

All reactions were carried out at 30 bar of hydrogen for 20 hrs at 80° C. at a S/C of 250.

Further reactions were carried out at 100° C. (Table 23).

TABLE 23

Asymmetric Hydrogenation of 1a-b at 100° C.

| Catalyst (mg) | Sub (mg) | S/C | Acid Acid/C | Time (h) | [S] mmol/mL | Conv (%) (254 nm) | Conv (%) (210 nm) | Ee (%) (210 nm) |
|---|---|---|---|---|---|---|---|---|
| Ru(R-C3-TunePhos)(acac)$_2$, 0.7 mg | 1a 46 | 250 | H$_3$PO$_4$ 63/1 | 20 | 0.1 | >99 | >99 | 90.1 (R) |
| Ru(S-C4-TunePhos)(acac)$_2$, 0.7 mg | 1a 46 | 250 | H$_3$PO$_4$ 63/1 | 20 | 0.1 | >99 | >99 | 91.4 (S) |
| [Ru(p-cymene)Cl$_2$]$_2$/S-C4-TunePhos, 0.24 mg/0.5 mg | 1a 47 | 250 | H$_3$PO$_4$ 63/1 | 20 | 0.1 | <5 | 5 | ND |
| [Ru(p-cymene)Cl$_2$]$_2$/S-C6-TunePhos 0.24 mg/0.5 mg | 1a 47 | 250 | H$_3$PO$_4$ 63/1 | 20 | 0.1 | <5 | <5 | ND |
| Ru(R-C3-TunePhos)(acac)$_2$, 0.7 mg | 1b 56 | | H$_3$PO$_4$ 63/1 | 20 | 0.1 | >99 $^1$H NMR | — | 89.5 (R) |
| Ru(S-C4-TunePhos)(acac)$_2$, 0.7 mg | 1b 55 | | H$_3$PO$_4$ 63/1 | 2 | 0.1 | >99 $^1$H NMR | — | 90.0 (S) |
| [Ru(p-cymene)Cl$_2$]$_2$/S-C4-TunePhos 0.24 mg/0.5 mg | 1b 56 | | H$_3$PO$_4$ 63/1 | 20 | 0.1 | <5 $^1$H NMR | — | ND |
| [Ru(p-cymene)Cl$_2$]$_2$/S-C6-TunePhos 0.24 mg/0.5 mg | 1b 56 | | H$_3$PO$_4$ 63/1 | 20 | 0.1 | <5 $^1$H NMR | — | ND |

All reactions were carried out at 30 bar of hydrogen at 100° C.

HPLC on the substrate 1b results showed ~5% unidentified byproducts.

Further reactions were carried out at 40° C. (Table 24).

TABLE 24

Asymmetric Hydrogenation of 1a-b at 40° C.

| Catalyst (mg) | Sub (mg) | Acid Acid/C | [S] mmol/mL | Conv (254 nm) | Conv % (210 nm) | Ee (%) (210 nm) |
|---|---|---|---|---|---|---|
| Ru(R-C3-TunePhos)(acac)$_2$, 0.7 mg | 1a 46 | H$_3$PO$_4$ 63/1 | 0.1 | >99 | >99 | 91.7 (R) |
| Ru(S-C4-TunePhos)(acac)$_2$, 0.7 mg | 1a 46 | H$_3$PO$_4$ 63/1 | 0.1 | >99 | >99 | 92.3 (S) |
| [Ru(p-cymene)Cl$_2$]$_2$/S-C4-TunePhos, 0.24 mg/0.5 mg | 1a 47 | H$_3$PO$_4$ 63/1 | 0.1 | <5 | <5 | ND |
| [Ru(p-cymene)Cl$_2$]$_2$/S-C6-TunePhos, 0.24 mg/0.5 mg | 1a 47 | H$_3$PO$_4$ 63/1 | 0.1 | <5 | <5 | ND |
| Ru(R-C3-TunePhos)(acac)$_2$, 0.7 mg | 1b 56 | H$_3$PO$_4$ 63/1 | 0.1 | >99 $^1$H NMR | — | 89.5 (R) |
| Ru(S-C4-TunePhos)(acac)$_2$, 0.7 mg | 1b 55 | H$_3$PO$_4$ 63/1 | 0.1 | >99 $^1$H NMR | — | 91.4 (S) |
| [Ru(p-cymene)Cl$_2$]$_2$/S-C4-TunePhos, 0.24 mg/0.5 mg | 1b 56 | H$_3$PO$_4$ 63/1 | 0.1 | <5 $^1$H NMR | — | ND |
| [Ru(p-cymene)Cl$_2$]$_2$/S-C6-TunePhos, 0.24 mg/0.5 mg | 1b 56 | H$_3$PO$_4$ 63/1 | 0.1 | <5 $^1$H NMR | — | ND |

All reactions were carried out at 30 bar of hydrogen for 20 hrs at 40° C. at a S/C of 250.

Asymmetric Hydrogenation of 1b and 1c

Using the standard conditions from the 1a testing, further testing was carried out on the substrates 1b and 1c (Tables 25 and 26, respectively).

TABLE 25

Asymmetric Hydrogenation of 1b

| Catalyst (mg) | Sub (mg) | Acid (mg) Acid/C | Conv (%) 1H NMR | Ee (%) (210 nm) |
|---|---|---|---|---|
| Ru(R-C3-TunePhos)(acac)2, 2.7 mg | 1b 86 | — | <5% | — |
| Ru(R-C3-TunePhos)(acac)2, 2.7 mg | 1b 86 | H3PO4 9.3 25/1 | >99 | 86.3 (R) |
| [Ru(R-C3-TunePhos)(p-cymene)Cl]Cl, 2.7 mg | 1b 86 | H3PO4 9.3 25/1 | >99 | 89.5 (R) |
| Ru(S-C3-Tune Phos)Cl2 (dmf)$_m$ 2.8 mg | 1b 87 | H3PO4 9.3 25/1 | >99 | 89.0 (S) |
| Ru(R-C3-Tune Phos)(CF3CO2)2, 2.8 mg | 1b 87 | — | >99 | 90.3 (R) |

All reactions were carried out under 30 bar hydrogen at 60° C. for 20 hrs using 0.1 mmol substrate per 1 mL of methanol. The ratio of sub/cat was 100.

TABLE 26

Asymmetric Hydrogenation of 1c

| Catalyst (mg) | Sub (mg) | TON | Acid (mg) Acid/C | [S] mmol/mL | Conv (%) (254 nm) | Conv (%) (210 nm) | Ee (%) (210 nm) |
|---|---|---|---|---|---|---|---|
| Ru(R-C3-TunePhos)(acac)$_2$, 2.7 mg | 1c 96 | 100 | — | 0.1 MeOH | 5 | 22 | 89.8 (R) |
| Ru(R-C3-TunePhos)(acac)$_2$, 2.7 mg | 1c 96 | 100 | H$_3$PO$_4$ 9.3 25/1 | 0.1 MeOH | 38 | 75 | 89.9 (R) |
| [Ru(R-C3-TunePhos)(p-cymene)Cl]Cl 2.7 mg | 1c 96 | 101 | H$_3$PO$_4$ 9.3 25/1 | 0.1 MeOH | 30 | 69 | 87.9 (R) |
| Ru(S-C3-Tune Phos)Cl$_2$(dmf)$_m$ 2.8 mg | 1c 97 | 100 | H$_3$PO$_4$ 9.3 25/1 | 0.1 MeOH | 25 | 62 | 87.5 (S) |
| Ru(R-C3-Tune Phos)(CF$_3$CO$_2$)$_2$ 2.8 mg | 1c 97 | 100 | — | 0.1 MeOH | 45 | 81 | 89.2 (R) |

All reactions were carried out under 30 bar hydrogen at 60° C. for 20 hrs.

Substrate Reactivity and Turnover Number (TON) Evaluation

A preliminary TON evaluation test was conducted (Table 27). Comparable results were achieved when TON increased to 1000.

TABLE 27

Asymmetric Hydrogenation of 1a - Preliminary TON Evaluation

| Catalyst (mg) | Sub (mg) | TON | Solvent (mL) | Conver (%) HPLC 254 nm | Ee (%) HPLC 254 nm | Conver (%) HPLC 210 nm | Ee (%) HPLC 210 nm |
|---|---|---|---|---|---|---|---|
| Ru(S-C3-TunePhos)(CF$_3$COO)$_2$, 2.9 mg | 768 | 1012 | MeOH 7 | >99 | 90.2 (S) | >99 | 90.0 (S) |

The reaction was carried out under 60 bar hydrogen at 70° C. for 19 hours.

Various ratios of substrate to catalyst were then investigated (Table 28).

TABLE 28

Asymmetric Hydrogenation of 1a - TON Evaluation

| Cat (mg) | Sub (mg) | S/Ru | H$_3$PO$_4$/ Cat | [S] mmol/mL | Conv (%) (254 nm) | Conv (%) (210 nm) | Ee (%) (210 nm) |
|---|---|---|---|---|---|---|---|
| 0.6 | 1a 323 | 2000 | 500 | 0.33 | 97 | >99 | 90.0 (R) |
| 0.6 | 1a 486 | 3000 | 750 | 0.5 | 97 | >99 | 89.2 (R) |

TABLE 28-continued

Asymmetric Hydrogenation of 1a - TON Evaluation

| Cat (mg) | Sub (mg) | S/Ru | H₃PO₄/Cat | [S] mmol/mL | Conv (%) (254 nm) | Conv (%) (210 nm) | Ee (%) (210 nm) |
|---|---|---|---|---|---|---|---|
| 0.6 | 1a 647 | 4000 | 1000 | 0.5 | 89 ¹H NMR | 83 | 89.3 (R) |
| 0.9 | 1a 730 | 3000 | 750 | 0.5 | >99 | >99 | 89.4 (R) |
| 0.4 | 1b 129 | 1000 | 250 | 0.1 | >99 ¹H NMR | — | 88.8 (R) |
| 0.4 | 1b 262 | 2000 | 500 | 0.2 | >99 ¹H NMR | — | 86.5 (R) |

All reactions were carried out at 30 bar of hydrogen for 20 hrs. Methanol was the solvent.

The product 2a crystallized out giving a reasonable amount after being stood out overnight (without lid) and the e.e. was >99%. It is envisaged that the e.e. of the product 2a may be easily upgraded to 99% e.e. using a crystallisation method.

Regarding substrate 1b, there was about 5% byproduct at higher temperature.

The preferred reaction conditions for substrate 1b involve the use of a Ru(S—C4-TunePhos)(acac)₂ catalyst at S/C 250 (Table 15). For substrate 1a, C3, C4, C5 and C6 TunePhos ligands give comparable results regarding conversion and ee. The preferred reaction conditions for substrate 1a are as follows: 0.5M 1a in methanol, isolated Ru(R—C3-TunePhos)(acac)₂ at S/C 3000, H₃PO₄/catalyst 750, 30 bar H₂, 80° C., 20 hours.

Scale-Up Experiments
Initial Experiments
The following reaction was investigated.

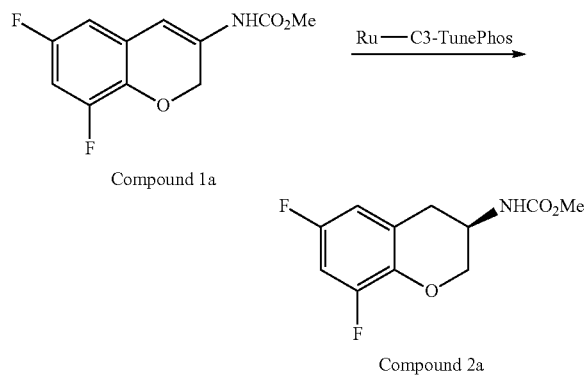

Compound 1a

Compound 2a

The hydrogenation was carried out in a 20 L vessel. The following materials and conditions were used:
Substrate (compound 1a): 950 g (3.94 mol);
Catalyst (Ru(R—C3-TunePhos)(acac)₂): 894 mg (3941 TON);
Acid additive (H₃PO₄) (85% aq.): 113 g (H₃PO₄/substrate=¼);
Solvent (MeOH): 5 L;
Temperature: 80-85° C.;
H₂ pressure: 30-35 bar;
The reaction was carried out for 24 hours, and cooled down to room temperature overnight naturally.

There was >99% conversion and 92.2% enantiomeric excess at 210 nm and >99% conversion and 93.0% enantiomeric excess at 254 nm.

The product was then separated and purified to provide a product with 99.9% enantiomeric excess and HPLC area (210 nm) >99%.

Follow-Up Experiments

A scale-up experiment was then carried out and the following materials and conditions were used.

TABLE 29

Raw Materials

| Key reagents | MW | Usage | Mol. | Molar Equivalent |
|---|---|---|---|---|
| Ene Carbamate 1 | 241.2 | 5000 g | 20.72 | 1.0 |
| R-C3 TunePhos Ru (acac)₂ | 908.0 | 6.28 g | 6.92 × 10⁻³ | 3.34 × 10⁻⁴ |
| H₃PO₄ (aq., 85%) | 98.00 | 600 g | 5.18 | 0.25 |
| H₂ (ultra high purity) | 2.02 | 30 bar | | |
| MeOH (99.8%) | 32.04 | 20 L | | |

Conditions:
TON 3000;
Temperature: 80-85° C.;
H₂ pressure: 30-35 bars.
Reaction volume 1 g/4 ml.
The general procedure was as follows:
1. Charge 20 L of methanol to the autoclave (stainless steel, T36).
2. Charge substrate to the autoclave.
3. Charge H₃PO₄ (85%) to the autoclave.
4. Purge the autoclave with nitrogen to replace the air inside.
5. Charge the ruthenium catalyst to the autoclave under nitrogen atmosphere.
6. Seal the reactor, and replace nitrogen with hydrogen (30 bar).
7. Heat the reaction mixture with stirring to 80° C. and hold at 80-85° C. for 24 hours while maintaining the pressure at 30-35 bars.
8. Cool the mixture to 25-30° C. and check the conversion (~100%).
9. Release the hydrogen pressure and purge the autoclave with nitrogen.
10. Transfer the suspension to the rotavap and concentrate to dryness under reduced pressure.
11. Dissolve the crude product in the mixture of isopropanol and water (45:55, v/v, 33.3 L) with stirring under reflux.
12. Cool the clear solution to room temperature and further cool to 0-5° C. and keep at 0-5° C. for 1 hour.
13. Collect the precipitate by filtration, and wash with the mixture of isopropanol and water (45:55, v/v, 7.5 L).
14. Dry the product at 50° C. in vacuum to constant weight.

Complete conversions were observed. The crude product was re-crystallized from IPA and water (45:55). After drying, total 4456 g of the pure product was obtained, which is a yield of 88.4%. The enantiomeric excess was >99% and the chemical purity (HPLC area) was >99% (210 nm).

Rhodium-Based Asymmetric Hydrogenation

Rhodium-DiPh-Me-BIPHEP Catalysis

The ligand DiPh-MeO-Biphep (compound I, below) was tested on substrates 1a-c.

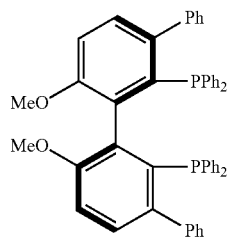

I

An in situ generated rhodium catalyst with DiPh-MeO-Biphep was tested and results are listed in Tables 30, 31 and 32.

TABLE 30

Asymmetric Hydrogenation of 1a - Rhodium Catalyst

| Catalyst (mg) | Sub (mg) | TON | Conver (%) HPLC 254 nm | Ee (%) HPLC 254 nm | Conver (%) HPLC 210 nm | Ee (%) HPLC 210 nm |
|---|---|---|---|---|---|---|
| Rh(NBD)$_2$PF$_6$/L* 1.8 mg/3.5 mg | 55 | 54 | 69 | 83.7 (R) | 92 | 83.4 (R) |

L* = DiPh—MeO-Biphep. Reactions was carried out in CH$_2$Cl$_2$, under 60 bar H$_2$ at room temperature for 18 hours

TABLE 31

Asymmetric Hydrogenation of 1a - Rhodium Catalyst

| Catalyst (mg) | Sub (mg) | TON | Solvent | Conver (%) HPLC 254 nm | Ee (%) HPLC 254 nm | Conver (%) HPLC 210 nm | Ee (%) HPLC 210 nm |
|---|---|---|---|---|---|---|---|
| Rh(NBD)$_2$PF$_6$/L* 1.8 mg/3.5 mg | 55 | 54 | CH$_2$Cl$_2$ | 69 | 83.7 (R) | 92 | 83.4 (R) |
| Rh(NBD)$_2$PF$_6$/L* 1.8 mg/3.4 mg | 59 | 58 | MeOH | 99 | 5.0 (R) | 99 | 4.3 (R) |
| Rh(NBD)$_2$PF$_6$/L* 1.7 mg/3.4 mg | 55 | 58 | PhMe | 95 | 77.1 (R) | 99 | 77.0 (R) |

L* = DiPh—MeO-Biphep. All reactions were carried out under 60 bar H$_2$ at room temperature for 18 hours Enantioselectivity was dependent on solvent and methylene chloride (CH$_2$Cl$_2$) was the most preferred solvent.

The activity and enantioselectivity were dependent on the hydrogen pressure. Higher pressure increases the activity, but slightly decreases the enantiomeric excess.

TABLE 32

Asymmetric Hydrogenation of 1a-c Catalyzed by in situ Rh/L*

| Sub | H$_2$ (bar) | Conv (%) (254 nm) | Conv (%) (210 nm) | Ee (%) (210 nm) |
|---|---|---|---|---|
| 1a | 10 | 99 | >99 | 92.0 (R) |
| 1a | 5 | 75 | 93 | 92.4 (R) |

TABLE 32-continued

Asymmetric Hydrogenation of 1a-c Catalyzed by in situ Rh/L*

| Sub | H$_2$ (bar) | Conv (%) (254 nm) | Conv (%) (210 nm) | Ee (%) (210 nm) |
|---|---|---|---|---|
| 1b | 10 | >99 $^1$H NMR | — | 91.4 (R) |
| 1b | 5 | 97 $^1$H NMR | — | ND |
| 1c | 10 | 99 | >99 | 92.6 (R) |
| 1c | 5 | 93 | 98 | 95.1 (R) |

All reactions were carried out at 60° C. for 20 hrs using 0.3 mmol substrate in 3 mL of methylene chloride. The catalyst was in situ formed with Rh(NBD)$_2$PF$_6$/DiPh-MeO-Biphep and the ratio of sub/Rh was 100.

Manufacture of Ru(R-C3-TunePhos)(acac)$_2$

To a three-neck flask was added 1088 mg of Ru(acac)$_3$, 3385 mg of zinc and 1620 mg of (R)—C3-TunePhos under nitrogen. The flask was evacuated and filled with nitrogen three times. To this flask was added air-free solvents 50 mL of ethanol and 5 mL of water under nitrogen. The mixture was then refluxed for 20 hours. The reaction mixture was cooled to room temperature and concentrated. To the residue was added 30 mL of acetone and the solution was filtered through a short pad of celite. The filtrate was concentrated providing 2.2 g of Ru(R—C3-TunePhos)(acac)$_2$ as a brown solid.

Manufacture of Ru(R—C3-TunePhos)(CF$_3$COO)$_2$

To a Schlenk flask was added 534.3 mg of [Ru(p-Cymene)Cl$_2$]$_2$, 1019 mg of (R)—C3-TunePhos and 15 mL of DMF. The solution was degassed three times using freeze-thaw method. Then the mixture was heated at 100° C. for 10 min. The reaction mixture was cooled to room temperature, then 2.86 g of NaOAc in 25 mL of methanol was added to the cooled reaction mixture. The mixture was stirred at room temperature for 30 min. To this resulting mixture was then added 25 mL of toluene and 25 mL of water. The two phases were separated and the aqueous phase was extracted with 2×12 mL of toluene. The combined organics were washed with 2×12 mL of water and dried over Na$_2$SO$_4$. The filtrate was concentrated providing a residue. To the residue were added 30 mL of methylene chloride and 270 mg of trifluoroacetic acid. The resulting mixture was stirred at room temperature for 24 h and concentrated to provide a greenish solid. This solid was dried under high vacuum overnight to yield 1.02 g of Ru(R—C3-TunePhos)(CF$_3$COO)$_2$.

Manufacture of Rh(norbornadiene)$_2$PF$_6$(DiPh-MeO-BIPHEP)

This catalyst may be formed in-situ by combining the individual ligands with a substrate and a solvent for the hydrogenation.

It will be appreciated that the invention may be modified within the scope of the appended claims.

The invention claimed is:

1. A process for preparing the S or R enantiomer of a compound of formula A,

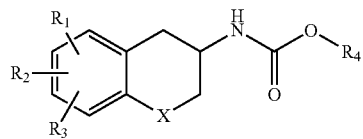

the process comprising subjecting a compound of formula B to asymmetric hydrogenation in the presence of a chiral transition metal catalyst and a source of hydrogen,

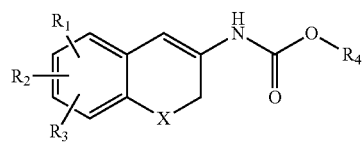

wherein X is CH$_2$, oxygen or sulphur; R$_1$, R$_2$ and R$_3$ are the same or different and signify hydrogens, halogens, alkyl, alkyloxy, hydroxy, nitro, alkylcarbonylamino, alkylamino or dialkylamino group; and R$_4$ is alkyl or aryl, wherein the transition metal catalyst comprises a chiral ligand having the formula

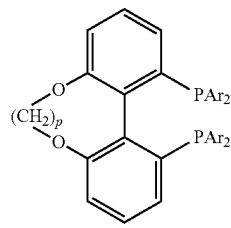

wherein p is from 1 to 6, and Ar means aryl group, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means an aromatic or heteroaromatic group, optionally substituted by alkyloxy, halogen or nitro group; and the term halogen means fluorine, chlorine, bromine or iodine.

2. The process according to claim 1, wherein X is O.

3. The process according to claim 1, wherein at least one of R$_1$, R$_2$ and R$_3$ is fluorine.

4. The process according to claim 1, wherein compound A has the following formula:

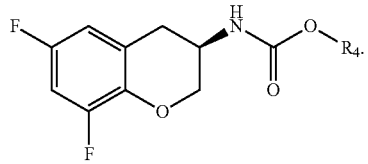

5. The process according to claim 1, wherein R$_4$ is C$_1$ to C$_4$ alkyl.

6. The process according to claim 1, wherein R$_4$ is benzyl.

7. The process according to claim 1, wherein p is 3, 4 or 5.

8. The process according to claim 1, wherein the chiral ligand is in the form of the R enantiomer or the S enantiomer.

9. The process according to claim 1, wherein the catalyst is selected from the group consisting of [Ru(p-cymene)(chiral ligand)Cl]Cl, [Ru(chiral ligand)Cl]$_2$(μ-Cl)$_3$(Me$_2$NH$_2$), [Ru(chiral ligand)Cl]$_2$(μ-Cl)$_3$(Et$_2$NH$_2$), Ru(chiral ligand)(BF$_4$)$_2$, Ru(chiral ligand)(OAc)$_2$, Ru(chiral ligand)(acetylacetonate)$_2$, Ru(chiral ligand)(CF$_3$COO)$_2$ and Ru(chiral ligand)Cl$_2$(dimethylformamide)$_m$, wherein m is 2, 3 or 4.

10. The process according to claim 1, wherein the hydrogenation is carried out in the presence of an acid.

11. The process according to claim 10, wherein a compound B/acid molar ratio ranges from 2/1 to 70/1.

12. The process according to claim 1, wherein a compound B/catalyst molar ratio ranges from 100/1 to 4000/1.

13. The process according to claim 1, wherein the hydrogenation is carried out in the presence of a solvent, and wherein the hydrogenation solvent is selected from a substituted or unsubstituted straight- or branched-chain C1 to C6 alcohol, an arene or mixtures thereof.

14. The process according to claim 1, wherein the hydrogenation is carried out at a temperature ranging from 40° C. to 100° C.

15. The process according to claim 1, wherein the hydrogenation is carried out at a pressure ranging from 10 bars to 70 bars.

16. A process for preparing the S or R enantiomer of a compound of formula A,

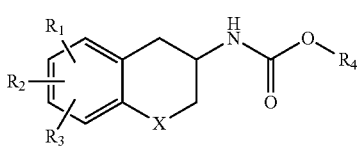

the process comprising subjecting a compound of formula B to asymmetric hydrogenation in the presence of a chiral transition metal catalyst and a source of hydrogen,

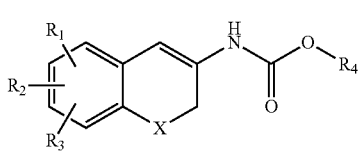

wherein X is CH$_2$, oxygen or sulphur; R$_1$, R$_2$ and R$_3$ are the same or different and signify hydrogens, halogens, alkyl, alkyloxy, hydroxy, nitro, alkylcarbonylamino, alkylamino or dialkylamino group; and R$_4$ is alkyl or aryl, wherein the transition metal catalyst comprises a DiPh-MeO-BIPHEP ligand having the formula J

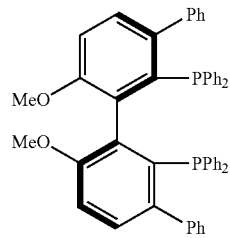

wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

17. The process according to claim 16, wherein the catalyst has the formula Rh(L")$_2$X/P*, wherein P* is the DiPh-MeO-BIPHEP ligand, L" is a diene and X is a counterion, wherein the diene is norbornadiene, cycloocladiene, or combinations thereof, and wherein the counterion is BF$_4$, PF$_6$, or combinations thereof.

18. A process for preparing the R or S enantiomer of a compound of formula C or salt thereof,

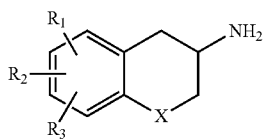

wherein X is CH$_2$, oxygen or sulphur; and R$_1$, R$_2$, R$_3$ are each selected from hydrogen, halogen, alkyl, alkyloxy, hydroxyl, nitro, amino, alkylcarbonylamino, alkylamino or dialkylamino, comprising forming the R or S enantiomer of a compound of formula A by a process according to claim 1, followed by converting the R or S enantiomer of the compound A to the respective R or S enantiomer of a compound of formula C.

19. The process for preparing the R or S enantiomer of a compound of formula E or a salt thereof:

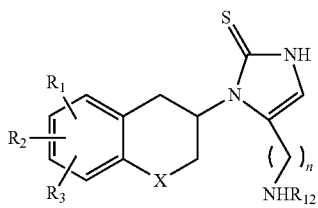

wherein X is CH$_2$, oxygen or sulphur; and R$_1$, R$_2$, R$_3$ are each selected from hydrogen, halogen, alkyl, alkyloxy, hydroxyl, nitro, amino, alkylcarbonylamino, alkylamino or dialkylamino, R$_{12}$ is selected from hydrogen, alkyl or alkylaryl, and n is 1, 2, or 3, the process comprising forming the R or S enantiomer of a compound of formula C by a process according to claim 18, and converting the R or S enantiomer of the compound of formula C to the R or S enantiomer of the compound of formula E.

20. The process according to claim 19, wherein the R or S enantiomer of the compound of formula C is reacted with a compound of formula D2

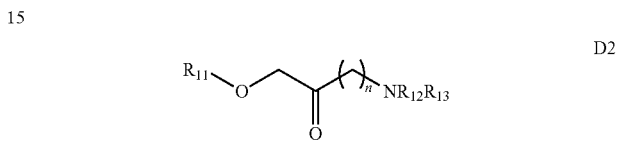

where n signifies 1, 2 or 3; when n is 1 or 2, R$_{12}$ signifies hydrogen, alkyl or alkylaryl group, R$_{11}$ signifies a hydroxyl protecting group and R$_{13}$ signifies an amino protecting group; when n signifies 3, R$_{11}$ signifies a hydroxyl protecting group but R$_{12}$ and R$_{13}$ taken together represent a phthalimido group; and with a water soluble thiocyanate salt in the presence of an organic acid in a solvent, followed by subsequent deprotection of one of the intermediate products F to I:

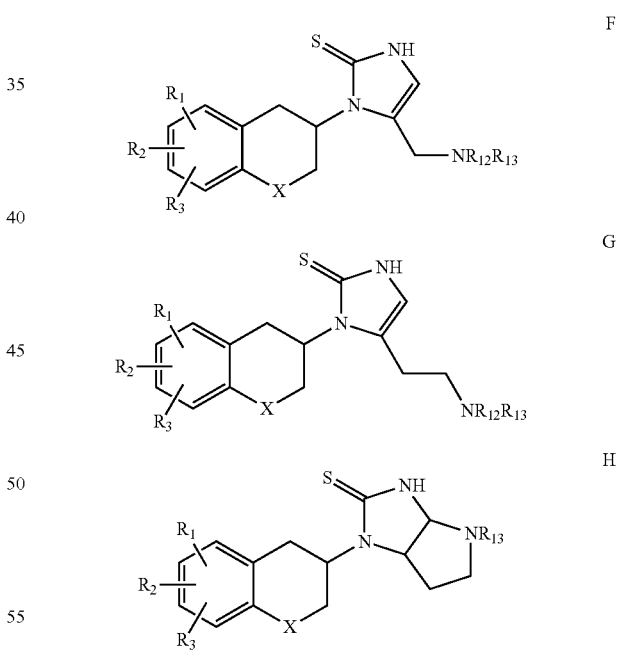

to give the compound of formula E.

21. The process according to claim 19, wherein the compound E is (S)-5-(2-aminoethyl)-1-(1,2,3,4-tetrahydronaphthalen-2-yl)-1,3-dihydroimidazole-2-thione; (S)-5-(2-aminoethyl)-1-(5,7-difluoro-1,2,3,4-tetrahydronaphthalen-2-yl)-1,3-dihydroimidazole-2-thione; (R)-5-(2-aminoethyl)-1-chroman-3-yl-1,3-dihydroimidazole-2-thione; (R)-5-(2-aminoethyl)-1-(6-hydroxychroman-3-yl)-1,3-dihydroimidazole-2-thione; (R)-5-(2-aminoethyl)-1-(8-hydroxychroman-3-yl)-1,3-dihydroimidazole-2-thione; (R)-5-(2-aminoethyl)-1-(6-methoxychroman-3-yl)-1,3-dihydroimidazole-2-thione; (R)-5-(2-aminoethyl)-1-(8-methoxychroman-3-yl)-1,3-dihydroimidazole-2-thione; (R)-5-(2-aminoethyl)-1-(6-fluorochroman-3-yl)-1,3-dihydroimidazole-2-thione; (R)-5-(2-aminoethyl)-1-(8-fluorochroman-3-yl)-1,3-dihydroimidazole-2-thione; (R)-5-(2-aminoethyl)-1-(6,7-difluorochroman-3-yl)-1,3-dihydroimidazole-2-thione; (R)-5-(2-aminoethyl)-1-(6,8-difluorochroman-3-yl)-1,3-dihydroimidazole-2-thione; (S)-5-(2-aminoethyl)-1-(6,8-difluorochroman-3-yl)-1,3-dihydroimidazole-2-thione; (R)-5-(2-aminoethyl)-1-(6,7,8-trifluorochroman-3-yl)-1,3-dihydroimidazole-2-thione; (R)-5-(2-aminoethyl)-1-(6-chloro-8-methoxychroman-3-yl)-1,3-dihydroimidazole-2-thione; (R)-5-(2-aminoethyl)-1-(6-methoxy-8-chlorochroman-3-yl)-1,3-dihydroimidazole-2-thione; (R)-5-(2-aminoethyl)-1-(6-nitrochroman-3-yl)-1,3-dihydroimidazole-2-thione; (R)-5-(2-aminoethyl)-1-(8-nitrochroman-3-yl)-1,3-dihydroimidazole-2-thione; (R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione; (R)-5-aminomethyl-1-(6-hydroxychroman-3-yl)-1,3-dihydroimidazole-2-thione; (R)-5-(2-aminoethyl)-1-(6-hydroxy-7-benzylchroman-3-yl)-1,3-dihydroimidazole-2-thione; (R)-5-aminomethyl-1-(6,8-difluorochroman-3-yl)-1,3-dihydroimidazole-2-thione; (R)-5-(3-aminopropyl)-1-(6,8-difluorochroman-3-yl)-1,3-dihydroimidazole-2-thione; (S)-5-(3-aminopropyl)-1-(5,7-difluoro-1,2,3,4-tetrahydronaphthalen-2-yl)-1,3-dihydroimidazole-2-thione; (R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione; (R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione, or a salt thereof.

22. The process according to claim 21, wherein the compound E is the respective R or S enantiomer of the compound of formula P:

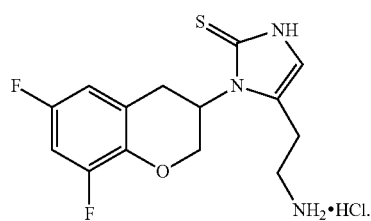

P

23. The process according to claim 1, wherein the catalyst is Ru(chiral ligand)(acetylacetonate)$_2$, wherein the chiral ligand is the R or S enantiomer of a compound having the formula

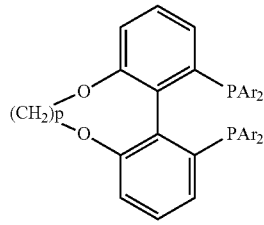

wherein p is an interger from 1 to 6.

24. The process according to claim 23, wherein p is 3, 4 or 5.

25. The process according to claim 1, wherein the catalyst is Ru(chiral ligand)(CF$_3$COO)$_2$, wherein the chiral ligand is the R or S enantiomer of a compound having the formula

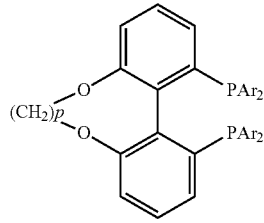

wherein p is an integer from 1 to 6.

26. The process according to claim 25, wherein p is 3, 4 or 5.

27. The process according to claim 1, wherein R$_4$ is methyl, ethyl or $^t$Bu.

28. The process according to claim 1, wherein R$_4$ is methyl.

29. The process according to claim 1, wherein the catalyst is Ru(chiral ligand)(acetylacetonate)$_2$ or Ru(chiral ligand)(CF$_3$COO)$_2$.

30. The process according to claim 1, wherein the hydrogenation is carried out in the presence of an acid selected from the group consisting of H$_3$PO$_4$, CF$_3$CO$_2$H and HOAc.

31. The process according to claim 23, wherein p is 3.

32. The process according to claim 25, wherein p is 3.

* * * * *

UNITED STATES PATENT AND TRADEMARK OFFICE
CERTIFICATE OF CORRECTION

PATENT NO. : 8,957,222 B2  
APPLICATION NO. : 12/921966  
DATED : February 17, 2015  
INVENTOR(S) : Alexander Beliaev, David Alexander Learmonth and Wenge Li Page 1 of 1

It is certified that error appears in the above-identified patent and that said Letters Patent is hereby corrected as shown below:

In the Claims:

Claim 1, Column 33, Line 57; Replace "Ar means arlyl group" with --Ar is phenyl--

Claim 16, Column 35, Line 3; Replace "nitro,_alkylcarbonylamino," with --nitro, alkylcarbonylamino,--

Claim 17, Column 35, Line 31; Replace "cycloocladiene" with --cyclooctadiene--

Claim 20, Column 36, Line 64; Replace "$R_{13}$." with --$R_{13}$,--

Signed and Sealed this  
Second Day of June, 2015

Michelle K. Lee  
*Director of the United States Patent and Trademark Office*